US006261778B1

(12) United States Patent
Tureci et al.

(10) Patent No.: US 6,261,778 B1
(45) **Date of Patent: *Jul. 17, 2001**

(54) ISOLATED NUCLEIC ACID MOLECULES WHICH ENCODE SCP PROTEINS, AND USES THEREOF

(75) Inventors: Ozlem Tureci; Ugur Sahin; Michael Pfreundschuh, all of Homburg/Saar (DE)

(73) Assignee: Ludwig Institute for Cancer Research, New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 09/411,812

(22) Filed: Oct. 1, 1999

Related U.S. Application Data

(63) Continuation-in-part of application No. 09/177,325, filed on Oct. 22, 1998.

(51) Int. Cl.[7] .............................. C12Q 1/68; C12P 21/00; G01N 33/18; H01L 21/00

(52) U.S. Cl. ............................... 435/6; 435/69.1; 436/64; 436/813; 438/7.23

(58) Field of Search ............................... 438/7.23; 435/6, 435/69.1; 436/64, 813

(56) References Cited

U.S. PATENT DOCUMENTS 5,888,751 * 3/1999 Tureci et al. ....................... 438/7.23

OTHER PUBLICATIONS

Offenberg et al., "SCP2: a major protein component of the axial elements of synaptonemal complexex of the rat", *Nucleic Acids Research*, vol. 20 (11), pp. 2572–2579, Apr. 1998.*

Rennert et al., "Regulated expression of Sterol Carrier Protein 2 in the Ovary: A key role for Cyclic AMP", *Biochemistry*, vol. 30, pp. 11280–11285, Sep. 1991.*

Muzny et al, "Homo sapiens Xp22 PACs RPC11–263P4 and RPC11–164K3 complete sequence", Genbank Accession NO: AC003046, Nov. 1997.*

Offenberg et al., "SCP2: a major protein components of the axial elements of synaptonemal complexes of the rat" *Nucleic Acids Research*, 1998, vol: 26, No: 11, pp. 2572–2579.

Worley, K.C., *GenCore*, 1997.

Hillier, et al., *GenCore*, 1997.

NCI–CGAP, *Gen Core*, 1997.

Stuhlmueller, et al., *GenCore*, 1996.

* cited by examiner

*Primary Examiner*—Jeffrey Fredman
*Assistant Examiner*—Arun K. Chakrabarti
(74) *Attorney, Agent, or Firm*—Fulbright & Jaworski, LLP

(57) ABSTRACT

The invention involves the recognition of a previously unidentified protein family which belongs to the human SCP family. The members of the family, such as SCP-2 and rat SCP-3 homolog, are markers for cell transformation. Also disclosed is the analysis of SCP proteins association with nuclear bodies. Diagnostic and therapeutic uses of these proteins and related molecules are taught.

14 Claims, No Drawings

SEQUENCE LISTING

<160> NUMBER OF SEQ ID NOS: 14

<210> SEQ ID NO 1
<211> LENGTH: 1116
<212> TYPE: DNA
<213> ORGANISM: Homo sapiens

<400> SEQUENCE: 1

```
aggaagtcct gcctgcagct ctcacgagaa ctgaggaccc gttttcttta cttttctttt     60

tttttgtttt tttgttttgt tttttttggg acggagtctg gctcttgctg cctaggctgc    120

agtgcagtgg tgtgatctgg gctcactgca acctccgcct cctgggttca agcaattctc    180

ctgcctcagc ttcctgagag gacccgtttt ctaagaggtc ctagtggtgc cgctgcctgc    240

aggttctttg agggcgccac atcaggggtc cctcaggttc ggggatcgcc tctagcttcc    300
```

-continued

```
caggacaacc agccacggat cctgtgggca ggagggctgc caaggcccag ttggaggctc    360

aatttatggc ggcctggggg aagaagcatg caggaaagga tccagtccgt gatgaatgtg    420

aggaaagaaa ccgttttaca gaaacaaggg aggaagatgt aactgatgag catggggaaa    480

gagaaccttt tgctgaaaca gatgaacaca cgggggctaa taccaagaag ccagaagata    540

ctgcagagga tcttactgca aaaagaaaaa ggatgaaaat ggataaaact tgcagcaaaa    600

caaagaacaa aagtaaacat gctttgagaa aaaagcaact taaaaggcag aaacgtgatt    660

atatacattc tctgaagttg ctaaatgtcc ttgaagaata catcacagac gagcagaaag    720

aggaagaaga agaagaggga gaagaggaag aactaattag aatatttcaa gaacaacaga    780

agaagtggca acaatataga agtgttagga gagagaggct gaaagagatg aagctgctac    840

gtgaccaatt cgtaaaggct cttgaggact ttgaagacct ttgtgacaga gtttttttccg    900

atgaagacag tgaacttgat aactagacat gtttttaaat aaaatcatgt cagaactctt    960

ttggaaaagt tggcacttac ccagttgtct cttcaacctc tgttattctg atgactgaag   1020

aaagaacttg aacctatgtt atatgataca agcacaactt gagctacagt aaactacatg   1080

acagtgtttt gataattgtt gtataaatcg gtatag                             1116
```

<210> SEQ ID NO 2
<211> LENGTH: 1276
<212> TYPE: DNA
<213> ORGANISM: Homo sapiens

<400> SEQUENCE: 2

```
gcctgcaggt tctgtgagga agcggcatca ggggtccctc aggttcaggg atcgcctcta     60

acttcccagg acagccaacc atggagcccg tgggcaggaa gcgcagcagg aaggctgcca    120

aagctcagtt ggaagctcaa gttacggccg cccagggggc cacgaaagaa ggttcaggga    180

tcgcctctaa cttcccagga cagccaacca tggagcccgt gggcaggaag cgcagcagga    240

aggctgccaa agctcagttg gaagctcaag ttagggccgc cccggcgaag aagcacacag    300

gaaaggatcc agtccgtgat gaatgtgagg aaagaaaccc ttttacagaa acaagggagg    360

aagatgtaac ttatgagcat ggggaaagag aacctttttgc tgaaaaagat gaacacacgg    420

ggattcatac catgaagcta gaacatattg cagctgacat tcaaaagggc cttgctgcaa    480

aaagagaaat gataaaaata gataaagcag cttacaggaa aaccaagaac acaattgaac    540

gtgctttgat aaaaaaacaa ctaaaaaggc agaaacgtga ttatagacat actcggaagt    600

tgctgaatgt ccttaaagaa tacatcgcag agaagcagaa agatgatgaa gcagaagaag    660

cagaagccgc agcagcagca gcggaagccg cagcagcagc agaagccgca gcagcagcag    720

cagaagtaat agtagtagaa gacgaagagg aggaagagaa ggaggaggag gaggagaaag    780

aagaggagga agaagaagga gaagaagaag gaggaggaga agaaggagaa gaaggaggag    840

gaggaggaga aggagaagaa acagaagaag aggaagagga agaagaagaa gaggaagagg    900

aagaacaaat taaagcattt caagaaaaac agaagaggtg gcaacaacct acaggtgtta    960

ggagctggag gctgagagag atgaagccgc tacttgagca attactaaag gctgccaagg   1020

acactaaaga caattattgc atcatttctt ccagtgaaga aagtgaactt gataactagc   1080

cgtgttttta aaaagaatcg tgtcagaact cttttggaag agttggcact tcattgtctc   1140

ttcaacctct gttattctga tgactgaaga aagaacttga acctatgtta tatgatacga   1200

gcacaacttg agctacagta aactacatga cagtgttttg ataattgttg tataaatcgg   1260

tatagctcct ctgtca                                                   1276
```

-continued

<210> SEQ ID NO 3
<211> LENGTH: 320
<212> TYPE: DNA
<213> ORGANISM: Homo sapiens

<400> SEQUENCE: 3

```
aatatttcaa gagcaacaaa agagacggca acaagatggg aaaggaactg aaagagattg     60

agccgccaca tgagcaattc acaaaggtct gaggacttgg aagagtataa tgaaagccct    120

ctttttggtg aagaaagtgg taaatttctt tttttgagac aactgcagta agagttggca    180

cttattcaga tgtctcttta accactgtta ttctgatggc tgatgaaaaa acttgaacct    240

atgttatatg atacaagcat aacttgagct acactaaacc acatgacagt atttagttaa    300

ttctcgtata aattagtgta                                                320
```

<210> SEQ ID NO 4
<211> LENGTH: 485
<212> TYPE: DNA
<213> ORGANISM: Homo sapiens

<400> SEQUENCE: 4

```
ggttcagagg tcgcctctag cttcccaggc cagtcagcca cggagcccgt gggcaggaag     60

ggcagcagga tggctgccaa ggaccagttg gaggttcaag ttatggccgc ccaggaaatg    120

gagcttgcag gaaaggatcc agtaagtcat gagcatgagg aaagaaaacc tgttacagag    180

acaaaggagg gagatgtaac tgatgagcat ggggaaagag gatcttttgc tgaaacagat    240

gaacacacgg gggttgatac caaggagcta gaagatattg cagctgacat taaagagcat    300

cttgctgcaa agagaaaaag gattgaaaag attgcaaaag cttgcagcga aataaagaac    360

agaattaaaa atgttttgag aacaacacaa ctaaaaaggc agaaacgtga ttatagaatt    420

tctctgaagt tgccgaatgt ccttgaagag ttcatcacag atgagcagaa agatgaggaa    480

ggaga                                                                485
```

<210> SEQ ID NO 5
<211> LENGTH: 24
<212> TYPE: DNA
<213> ORGANISM: Homo sapiens

<400> SEQUENCE: 5

```
acagaagtgt ctaggattca ttca                                            24
```

<210> SEQ ID NO 6
<211> LENGTH: 21
<212> TYPE: DNA
<213> ORGANISM: Homo sapiens

<400> SEQUENCE: 6

```
gaagaggtgg caacaatata g                                               21
```

<210> SEQ ID NO 7
<211> LENGTH: 407
<212> TYPE: DNA
<213> ORGANISM: Homo sapiens

<400> SEQUENCE: 7

```
cagtgaattg taatacgact cactataggg cgaattgggc cctctagatg catgctcgag     60

cggccgccag tgtgatggat atctgcagaa ttcggcttga agaggtggca acaatatagc    120
```

-continued

```
attgttagga gacagcaaat gaaagagatt aagctgctat atgagcaatt cacgaagagt    180

atcatgaaag aactcttttc agtgaagaaa gtcaatttaa atcgccaagt tccaagataa    240

aattgtgtga gagacactgc agcaagagtt ggcactaatt cataacttga gctacactaa    300

accacatgac agtattttga tattcttgta taaaccagtt tatttcttct atcattagtc    360

tgttaaatgc cagacctcat ttctgtggtc tgttgaatga atcctag                  407


<210> SEQ ID NO 8
<211> LENGTH: 21
<212> TYPE: DNA
<213> ORGANISM: Homo sapiens

<400> SEQUENCE: 8

acctacaggt gttaggagct g                                               21


<210> SEQ ID NO 9
<211> LENGTH: 21
<212> TYPE: DNA
<213> ORGANISM: Homo sapiens

<400> SEQUENCE: 9

acagaggttg ttgagacaat g                                               21


<210> SEQ ID NO 10
<211> LENGTH: 21
<212> TYPE: DNA
<213> ORGANISM: Homo sapiens

<400> SEQUENCE: 10

gcagaaacgt gattatagaa t                                               21


<210> SEQ ID NO 11
<211> LENGTH: 21
<212> TYPE: DNA
<213> ORGANISM: Homo sapiens

<400> SEQUENCE: 11

ggttgaagat acatctgaat a                                               21


<210> SEQ ID NO 12
<211> LENGTH: 4967
<212> TYPE: DNA
<213> ORGANISM: Homo sapiens

<400> SEQUENCE: 12

aaatgaagtc aaaatgccaa taagaccaga tctccagcag ttggaaaaat gcattgatga     60

tgctttaaga aaaaatgatt tcaaaccttt gaaaacactt ttgcaaattg atatttgtga    120

agatgtgaag attaaatgca gcaaacagtt tttccacaag gtggacaacc ttatatgcag    180

ggaacttaat aaagaggata tccacaatgt ttcagccatt ttggtttctg ttggaagatg    240

tggcaaaaat atcagtgtat tggggcaagc tggacttcta acgatgataa aacaaggact    300

aatacaaaag atggttgcct ggtttgaaaa atccaaggac attattcaga gtcaaggaaa    360

ttcaaaagat gaagctgttc taaatatgat agaagactta gttgatcttc tgctggtcat    420

acatgatgtc agtgatgaag gtaaaaaaca agtagtggaa agtttcgtac ctcgcatttg    480

ttccctggtt attgactcaa gagtgaatat ttgtattcag caagagatta taaaaaaaat    540

gaatgctatg cttgacaaaa tgcctcaaga tgcccggaaa atactctcta accaagaaat    600

gttaattctc atgagtagta tgggagaaag gattttagat gctggagatt atgacttaca    660
```

-continued

```
ggtagccatt gtagaagctt tgtgtagaat gaccacagaa aaacaaagac aagaactggc    720
acatcagtgg ttttcaatgg attttattgc taaggcattt aaaagaatta aggactctga    780
atttgaaaca gattgcagga tatttctcaa ccttgtaaat ggcatgcttg gagacaaaag    840
aagggtcttt acatttcctt gtttatcagc atttcttgat aaatatgagc tgcaaatacc    900
atcagatgaa aaacttgagg aattttggat tgattttaat cttgggagtc agactctctc    960
attctacatt gctggagata atgatgatca tcaatgggaa gcagttactg tgccagagga   1020
aaaagtacaa atatacagca ttgaagtgag agaatcaaag aagctactga caataattct   1080
gaaaaataca gtaaaaatta gcaaaagaga agggaaagaa ttgcttttgt attttgacgc   1140
atcactagaa atcactaatg taactcaaaa aatttttggt gcaactaaac atagggaatc   1200
tatcagaaaa caaggtattt cagttgccaa aacgtcgctg catatacttt ttgacgcaag   1260
tggatcacag attctagtgc cagaaagtca aatctcacca gtcggagaag agctcgttag   1320
tttaaaggaa aaatcaaagt ccccaaagga atttgctaaa ccttcaaaat atatcaaaaa   1380
cagtgacaaa gggaatagaa ataatagtca gcttgagaaa actactccta gcaaaagaaa   1440
aatgtctgaa gcatcaatga ttgtttctgg tgcagataga tacactatga gaagtccagt   1500
gcttttcagc aacacatcaa taccaccacg aagaagaaga attaaaccac cactgcaaat   1560
gacgagctct gcagagaaac ctagtgtttc tcaaacatca gaaaatagag tggataatgc   1620
tgcatcactg aaatctagat catcagaagg aagacataga agagataata tagacaaaca   1680
tatcaaaact gctaagtgtg tagaaaacac agaaaataag aatgttgaat tcccaaacca   1740
aaattttagt gaactccagg atgttatacc agattcacag gcagcggaaa aaagagatca   1800
tactatatta cctggtgttt tagacaacat ctgtggaaat aaaatacaca gcaaatgggc   1860
atgttggaca cctgtaacaa acattgaact atgtaataac caaagagcaa gtacttcgtc   1920
aggagacaca ttgaatcaag atattgttat aaataaaaaa cttactaaac aaaaatcatc   1980
ctcttcaata tctgatcata attctgaagg aacaggaaaa gtgaaatata agaaagaaca   2040
aaccgaccat atcaaaatag ataaagcaga agtagaagtt tgcaggaaac acaatcagca   2100
acaaaatcat cctaaatatt cagggcagaa aaatactgaa aatgccaagc agagtgattg   2160
gcctgttgaa tctgaaacta cttttaaatc ggttctccta aataagacaa ttgaagaatc   2220
gctgatatat aggaagaaat acatattgtc aaaagatgtg aatactgcta cttgcgataa   2280
aaatccatct gctagcaaaa atgtgcaaag tcatagaaaa gcagagaaag aattgacttc   2340
tgagcttaat tcctgggatt cgaaacaaaa aaaaatgaga gaaaagtcaa aagggaaaga   2400
atttaccaat gtagcagaat ccttgataag ccaaatcaat aaaagataca aaacaaaaga   2460
tgacatcaag tctacaagaa aattaaagga gtctttgatt aacagtggtt tttcaaacaa   2520
acctgttgta caactcagta aggaaaaagt tcagaaaaaa agctacagaa aactgaagac   2580
tacctttgtt aatgttactt ctgaatgccc agtgaatgat gtttacaatt ttaatttgaa   2640
tggagctgat gaccctatca taaaacttgg aatccaagag tttcaagcta cagctaaaga   2700
agcttgtgcg gataggtcaa ttagattggt aggtccaagg aatcatgatg aacttaaatc   2760
ttctgtcaaa acaaaagata aaaaaattat aacaaatcat caaaagaaaa atctgtttag   2820
tgatactgaa acagagtaca gatgtgatga cagcaagact gatattagct ggctaagaga   2880
accgaaatca aaaccacagc taatagacta tagcagaaat aaaaatgtga agaatcataa   2940
aagtggaaaa tcaagatcat ccttggaaaa gggacagcca agctctaaaa tgacacccag   3000
```

-continued

```
taaaaatatc acaaaaaaga tggacaagac aattccggaa ggaagaatca gacttccacg   3060
aaaagcaacc aaaacaaaaa aaaactataa agatctctca aattcagaat cagagtgtga   3120
acaagaattt tcacattcat ttaaagagaa cataccagta aaggaggaga atatccattc   3180
cagaatgaaa acggtaaagc taccaaagaa acaacagaaa gtcttctgtg ctgaaacaga   3240
aaaggaacta tcaaaacaat ggaaaaactc atctctacta aaagatgcta tacgagataa   3300
ttgccttgac ttatctccca gatctttatc tggcagtcca tcatctatag aagtaacgag   3360
atgtatagag aaaataacag aaaaggattt tactcaggat tatgactgca taacaaaatc   3420
tatatcacct tatccaaaaa cttcatcact tgaatcctta aatagtaaca gtggagttgg   3480
aggtacaata aagtcaccca aaaacaatga gaaaaacttc ctgtgtgcaa gtgaaagttg   3540
ttcaccaact ccacgaccac tgtttttggc cagacatact ccaactaaga gtaatactat   3600
tgtaaataga aaaaaaataa gttctctggt acttacacaa gaaacacaaa acagtaacag   3660
ctattcagat gtaagcagat atagttcaga agaacggttt atggaaattg aatctccaca   3720
tatcaatgaa aattatatac aaagcaaaag agaggaaagt catttagcat cttcattatc   3780
caagtctagt gaaggaagag agaaaacgtg gtttgacatg ccctgtgatg ctactcatgt   3840
atcaggcccc acccaacatc ttagtcgcaa aagaatatat atagaagata atctaagtaa   3900
ttccaatgaa gtagaaatgg aagagaaagg agaaaggaga gcaaacttgc ttcccaaaaa   3960
actgtgtaaa attgaagatg cagatcatca tatccacaaa atgtctgaaa gtgtatcttc   4020
attatcaaca aatgactttt ctattccttg ggagacctgg caaaatgaat ttgcagggat   4080
agagatgact tatgagactt acgagaggct caattcagaa tttaagagaa ggaataatat   4140
ccgacataaa atgttgagtt attttactac gcagtcttgg aaaacagctc agcaacatct   4200
gagaacaatg aatcatcaaa gtcaggactc taggattaaa aacttgata aattccaatt   4260
cattatcata gaggagctgg agaattttga aaaagattca cagtctttaa aagatttgga   4320
aaaggaattt gtggactttt gggaaaagat atttcagaag ttcagtgcat atcaaaaaag   4380
cgaacaacag aggcttcatc ttttgaaaac ttcattggct aaaagtgtct tctgtaatac   4440
tgatagtgaa gaaactgttt ttacatccga gatgtgtttg atgaaagaag atatgaaagt   4500
gctgcaagac aggcttctta aggacatgct agaagaggag cttcttaatg tacgcagaga   4560
actgatgtca gtattcatgt ctcatgaaag aaatgctaat gtgtgaaatc tagtttttat   4620
caccatactt tatctaatta ttattctctg tatataactg aggaaataag aatagtccta   4680
caaagagaaa aatatacatg tcaccgaagc aagtgtaccc tttataggaa ccctcaaatt   4740
aaaaaaaaat gtcttttaat ggatgagagg gaaccactat aacatgagtc caagcccaga   4800
agacttctgt ctatacaata tttttttta attttggaga taaaagcttt aagaaacttt   4860
ttgagttaat tatactcata aaatgagttt ctttaataaa ttaaatttta ttgtgtaaaa   4920
tgtattatta cataaaatgt gtttttgaat caatgcagtt tgggccg                 4967
```

<210> SEQ ID NO 13
<211> LENGTH: 27
<212> TYPE: DNA
<213> ORGANISM: Homo sapiens

<400> SEQUENCE: 13

```
gattcggcac gcaggggatg ttatacc                                         27
```

<210> SEQ ID NO 14
<211> LENGTH: 27

-continued

```
<212> TYPE: DNA
<213> ORGANISM: Homo sapiens

<400> SEQUENCE: 14

gccaatcact ctgcttggca ttttcag                                  27
```

ISOLATED NUCLEIC ACID MOLECULES WHICH ENCODE SCP PROTEINS, AND USES THEREOF

This application is a continuation-in-part of co-pending application Ser. No. 09/177,325 filed Oct. 22, 1998 incorporated herein by reference.

FIELD OF THE INVENTION

The invention relates to the identification of a molecule or a marker for transformed cells, such as cancer. It also relates to a method for identifying molecules associated with pathological conditions, such as cancer.

BACKGROUND AND PRIOR ART

It is fairly well established that many pathological conditions, such as infections, cancer, autoimmune disorders, etc., are characterized by the inappropriate expression of certain molecules. These molecules thus serve as "markers" for a particular pathological or abnormal condition. Apart from their use as diagnostic "targets", i.e., materials to be identified to diagnose these abnormal conditions, the molecules serve as reagents which can be used to generate diagnostic and/or therapeutic agents. A by no means limiting example of this is the use of cancer markers to produce antibodies specific to a particular marker. Yet another non-limiting example is the use of a peptide which complexes with an MHC molecule, to generate cytolytic T cells against abnormal cells.

Preparation of such materials, of course, presupposes a source of the reagents used to generate these. Purification from cells is one laborious, far from sure method of doing so. Another preferred method is the isolation of nucleic acid molecules which encode a particular marker, followed by the use of the isolated encoding nucleic acid molecule to express the desired protein molecule.

To date, two strategies have been employed for the detection of such antigens, in e.g., human tumors. These will be referred to as the genetic approach and the biochemical approach. The genetic approach is exemplified by, e.g., dePlaen et al., *Proc. Nat. Acad. Sci. USA* 85: 2275 (1988), incorporated by reference. In this approach, several hundred pools of plasmids of a cDNA library obtained from a tumor are transfected into recipient cells, such as COS cells, or into antigen-negative variants of tumor cell lines. Transfectants are screened for the expression of tumor antigens via their ability to provoke reactions by anti-tumor cytolytic T cell clones. The biochemical approach, exemplified by, e.g., Mandelboim, et al., *Nature* 369: 69 (1994) incorporated by reference, is based on acidic elution of peptides which have bound to MHC-class I molecules of tumor cells, followed by reversed-phase high performance liquid chromatography (HPLC). Antigenic peptides are identified after they bind to empty MHC-class I molecules of mutant cell lines, defective in antigen processing, and induce specific reactions with cytotoxic T-lymphocytes. These reactions include induction of cytolytic T cell lines (CTLs) proliferation tumor necrosis factor (TNF) release, and lysis of target cells, measurable in an MTT assay, or a $^{51}$Cr release assay.

These two approaches to the molecular definition of antigens have the following disadvantages: first, they are enormously cumbersome, time-consuming and expensive; second, they depend on the establishment of CTLs with predefined specificity; and third, their relevance in vivo for the course of the pathology of disease in question has not been proven, as the respective CTLs can be obtained not only from patients with the respective disease, but also from healthy individuals, depending on their T cell repertoire.

The problems inherent to the two known approaches for the identification and molecular definition of antigens is best demonstrated by the fact that both methods have, so far, succeeded in defining only very few new antigens in human tumors. See, e.g., van der Bruggen et al., *Science* 254: 1643–1647(1991); Richard et al., *J. Exp. Med.* 178: 489–495 (1993); Coulie, et al., *J. Exp. Med.* 180: 35–42 (1994); Kawakami, et al., *Proc. Natl. Acad. Sci. USA* 91: 3515–3519 (1994).

Further, the methodologies supra described rely on the availability of established, permanent cell lines of the cancer type under consideration. It is very difficult to establish cell lines from certain cancer types, as is shown by, e.g., Oettgen, et al., *Immunol. Allerg. Clin. North. Am.* 10: 607–637 (1990). It is also known that some epithelial cell type cancers are poorly susceptible to CTLs in vitro, thus precluding routine analysis. These problems have stimulated the art to develop additional methodologies for identifying cancer associated antigens.

One key methodology is described by Sahin, et al., *Proc. Natl. Acad. Sci. USA* 92: 11810–11913 (1995), incorporated by reference. Also, see U.S. Pat. No. 5,698,396, and application Ser. No. 08/479,328, filed on Jun. 7, 1995 and Jan. 3, 1996, respectively (both incorporated by reference.) To summarize, the method involves the expression of cDNA libraries in a prokaiyotic host. (The libraries are secured from a tumor sample.) The expressed libraries are then immunoscreened with absorbed and diluted sera, in order to detect those antigens which elicit high titer humoral responses. This methodology is known as the SEREX method ("Serological identification of antigens by Recombinant Expression Cloning"). The methodology has been employed to confirm expression of previously identified tumor associated antigens, as well as to detect new ones. See the above referenced patent applications and Sahin, et al., supra, as well as Crew, et al., *EMBO J*, 144: 2333–2340 (1995).

The SEREX methodology has been applied to esophageal cancer samples, and an esophageal cancer associated antigen has now been identified, and its encoding nucleic acid molecule isolated and cloned, as per U.S. patent application Ser. No. 08/725,182, filed Oct. 3, 1996, incorporated by reference herein.

The relationship between some of the tumor associated genes and a triad of genes, known as the SSX genes, is under investigation. See Sahin, et al., supra; and Tureci, et al., *Cancer Res.*, 56:4766–4772 (1996). One of these SSX genes, referred to as SSX2, was identified, at first, as one of two genes involved in a chromosomal translocation event (T(X; 18)(p 11.2; q 11.2)), which is present in 70% of synovial sarcomas. See Clark, et al., *Nature Genetics*, 7:502–508 (1994); Crew et al., *EMBO J.*, 14:2333–2340 (1995). This gene was later found to be expressed in a number of tumor cells, and is now considered to be a tumor associated antigen referred to as HOM-MEL-40 by Tureci, et al, supra. Its expression to date has been observed in cancer cells, and normal testis only. This parallels other members of the "CT" family of tumor antigens, since they are expressed only in cancer and testis cells. Crew et al. also isolated and cloned the SSX1 gene, which has 89% nucleotide sequence homology with SSX2. See Crew et al., supra. Additional work directed to the identification of SSX genes has resulted in the identification of SSX3, as is described by DeLeeuw, et al., *Cytogenet. Genet.*, 73:179–183 (1996). The fact that SSX presentation parallels other CT antigens suggested to the inventors that other SSX genes might be isolated.

Application of a modification of the SEREX technology described supra has been used, together with other techniques, to clone two, additional SSX genes, referred to as SSX4 and SSX5 as alternate splice variants of the SSX4 gene. This work is described in U.S. Ser. No. 08/851,138, filed May 5, 1997, incorporated by reference, as well as by Chen, et al., *Proc. Natl. Acad. Sci USA*, 94: 1914–1918 (1997), also incorporated by reference.

The fact that many markers were found in both normal testis and tumor cells, but not other normal cells, suggested that further investigation in this area might uncover additional related molecules. The diversity of those discovered so far, however, did not provide any guidance as to the characteristics of the additional molecules which might be found.

Most of the work prior to the invention disclosed herein, used cDNA libraries obtained from cancer cells. As will be developed herein, it has now been shown that such molecules can also be determined using a non-transformed, or normal cell source for the cDNA libraries previously obtained from cancer cells. This is quite surprising, as it might well be assumed that tumor markers are expressed only in tumor cells. This has now been shown to not be the case. Exemplary of a normal cell library which can be used is a testis cell library screened against various serum samples, such as autologous serum.

Synaptonemal complex protein 1 ("SCP-1" hereafter) is a protein involved in the meiotic prophase of spermatocytes. The gene which encodes murine SCP-1 has been mapped to chromosome 1p.12–p.13. See Sage, et al., *Biochem. Biophys. Acta* 1263: 258–260 (1995) incorporated by reference. The human form of SCP-1 has been reported to be expressed only in testis. See Meuwissen, et al, *EMBO J* 11:5091–5100 (1992), incorporated by reference.

Meuwissen et al, supra describe SCP-1 protein as a major component of the synaptonemal complex, a tripartite, macromolecular assembly which is formed between homologous chromosomes during meiotic prophase. See Wettstein, et al., *Annu. Rev. Genet* 3:331–413 (1984); Heyting, et al., *Genome* 31:81–89 (1986). More details of the protein may be found, e.g., in Meuwissen, et al., *Genomics* 37:101–106 (1997); Gillies, et al., *Curr. Trac. Lab. Carlsberg* 40:135–161 (1975); Schmekel, et al., *Exp. Cell Res* 226:20–30 (1996); Moses, et al., *Symp. Soc. Exp. Biol.* 38:245–270 (1984); Carpenter, *Bioessays* 6:232–236 (1987); Loidl, et al., *Genome* 33:759–778 (1990); Moens, *Bioessays* 16:101–106 (1994); Roeder, *Trends Genet* 6:385–389 (1990).

The location of the gene for SCP-1 is different than that for all previously identified cancer testis antigens (CTAs), which map to the X chromosome.

In allowed U.S. application Ser. No. 08/892,702, filed Jul. 15, 1997 now U.S. Pat. No. 5,888,751, and incorporated by reference, it was shown that SCP-1 is expressed in tumor cells, especially in renal cell carcinomas, gliomas, and breast carcinomas, but not in normal cells except for testis. Hence, it serves as a CTA but differs in that it possesses strong expression not only in melanoma, but in those tumor types listed supra.

This is significant in terms of both diagnostic and therapeutic approaches to transformed cells, as will be seen from the disclosure which follows. The fact that the molecule is also involved in normal meiosis suggested an important correlation between the molecule, chromosomal replication, cell division, and the onset of oncogenesis.

The SCP-1 gene was found to be testis specific, in that the only normal cells in which it was expressed were testis. Additional research has now been carried out, and additional isolated nucleic acid molecules have been identified which serve as cancer markers, but the only normal cells in which they are expressed are testis cells. More detailed information on these molecules, their localization within the cell, their colocalization with other proteins in nuclear bodies, and their use is set forth in the disclosure which follows.

DETAILED DESCRIPTION OF PREFERRED EMBODIMENTS

EXAMPLE 1

An electronic search of the Genbank database was carried out to identify known nucleic acid molecules which belong to the synaptonemal complex described supra. Specifically, the search criteria were testis specific expression, and association with meiosis. The result of this search yielded a non-homologous sequence, for rat SCP-3. No human counterpart was found; however, a rat SCP-3 sequence was identified, and was then used to search for homologous sequences in the human expression sequence tag ("EST") databases. Two sequences were identified. The search was a BLAST search of the DBEST database. "BLAST" is an acronym for Basic Local Alignment Search Tool. DBEST is a database of EST sequences. These have access numbers AA431205 and AA431529 in the sequence libraries. Both were reported as having come from a testis library. These publicly available sequences are incorporated by reference.

The AA431205 sequence was used to design a primer for RACE analysis in accordance with Frohman , et al., *Meth. Enzymol* 218: 340–356 (1993), incorporated by reference. Two rounds of RACE were carried out, using an anchor primer and ACAGAAGTGTCTAGGATTCA TTCA (round 1), then the anchor primer and GACAGAGGAGCTATACCGATTTATAC. The primer was used to screen a testicular library, and two transcripts were identified. These are referred to as SEQ ID NO: 1 (SCP-3A), and SEQ ID NO: 2 (SCP-3B) hereafter. These sequences were then compared to sequences in the Genbank library, using BLAST. Two highly homologous sequences were identified, referred to as gbAC 002366 and gbAC 003046. Both of these are sequences reported by the human genome project, as coming from human chromosome X. The former is a cosmid from region Xp22, while the latter is a PAC from Xp22 RPC11-263P4. Both of these library items represent genomic DNA sequences. Using exon/intron determination rules, SEQ ID NOS: 3 and 4 were determined, as being expressed or translated portions. The former corresponds to the 3'-end of a gene homologous to SEQ ID NOS: 1 and 2, while the latter sets forth an entire gene sequence which is homologous to SEQ ID NOS: 1 and 2 as well.

EXAMPLE 2

The information from AA431205, which was 518 base pairs long was used to study expression in normal and cancer tissues. Two oligonucleotide primers were prepared, based upon the sequence information, and were used in assays, described infra.

The oligonucleotide primers were:

ACAGAAGTGT CTAGGATTCA TTCA (SEQ ID NO: 5, sense) and

GAAGAGGTGG CAACAATAT AG (SEQ ID NO: 6 antisense), respectively.

RT-PCR was then carried out, using these primers, for 35 cycles (one cycle: (60° C. for one minute, 72° C. for two minutes, 94° C. for one minute), preceded by 12 minutes at 94° C. followed by a final "cycle" of 72° C. for 8 minutes.

No expression was found in any normal tissue tested except testis; however, PCR product was found in prostate, breast, ovarian, and renal cell carcinoma cancer tissues.

In addition to products of the expected size, aberrant smaller products were found in breast cancer samples. One of these aberrant clones was sequenced, and the sequence is set forth at SEQ ID NO: 7. While different from all of SEQ ID NOS: 1, 2, 3, and 4, it is related to these sequences.

EXAMPLE 3

In experiments not reported here, it was found that of normal tissue samples, only testis was positive for any of the sequences under consideration. In addition to SEQ ID NOS: 5 & 6, which were used to analyze for SEQ ID NO: 1, primers:

5'-ACCTACAGGT GTTAGGAGCT G-3' (SEQ ID NO: 8) and

5'-ACAGAGGTTG TTGAGACAAT G-3' (SEQ ID NO: 9)

were used, as sense and antisense to determine SEQ ID NO: 2. The RT-PCR for analyzing the samples involved 12 minutes of denaturing, followed by 35 cycles of 1 minute at 60° C., 2 minutes at 72° C., and 1 minute at 94° C., followed by 35 cycles of 1 minute at 94° C.

The samples which were negative included stomach, muscle, colon, lung, breast, liver, prostate, kidney, skin, and brain.

EXAMPLE 4

The RT-PCR protocols given supra were then used, with SEQ ID NOS: 5&6 or 10&11, to determine expression in cancer. The results are as follows, expressed as "x/y", where "x" is the number of positive samples, and "y" is the total number analyzed. SEQ ID NO: 4 was detected using:

5'GCAGAAACGT GATTATAGAA-T-3' (SEQ ID NO: 10) and

5'-GGTTGAAGAT ACATCTGAAT A-3' (SEQ ID NO: 11)

| CANCER TYPE | SEQ ID NO: 1 | SEQ ID NO: 4 |
|---|---|---|
| Prostate | 4/26 | 0/26 |
| Renal Carcinoma | 2/23 | 1/15 |
| Melanoma | 4/18 | 3/12 |
| Melanoma Cell Lines | 1/5 | not done |
| Ovarian | 0/25 | 6/25 |
| Breast | 0/10 | 2/15 |
| Colorectal | 0/10 | 0/10 |
| Lung | 0/8 | 0/8 |

When the primers and conditions of example 3 were used, SEQ ID NO: 7 was found in breast cancer.

EXAMPLE 5

The work set forth supra deals with human nucleic acid molecules with homology to rat SCP-3. Recently Offenburg et al., *Nucl. Acids, Res.*, 26(11): 2572–2579 (1998), the disclosure of which is incorporated by reference, disclosed human SCP2. This sequence is presented as SEQ ID NO: 12. It is publicly available via Genbank accession number γ08982, incorporated by reference. As with SCP-1 and SCP-3, the SCP gene was described as being expressed specifically in testis, but was not associate with cancer.

Following study of the SCP2 sequence, primers were designed for RT-PCR. These were:

5'-GATTCGGCAC GCAGGGGATG TTATACC-3' (SEQ ID NO: 13) and

5'-GCCAATCACT CTGCTTGGCA TTTTCAG (SEQ ID NO: 14)

which served as sense, and antisense primers, respectively.

RT-PCR was carried out in total cellular RNA which had been extracted, and screened with oligos, and then reverse transcribed.

The PCR was carried out by heating the cDNA for 2 minutes at 95° C., followed by 35 cycles of 1 minute at 60° C., 2 minutes at 72° C., and one minute at 94° C.

The RT-PCR was carried out on normal stomach, muscle, colon, lung, breast, liver, prostate, kidney, skin, brain and testis tissues. Only testis was positive.

Tumor samples were also analyzed. The results follow expressed as "x/y", where "x" is the number of positive samples, and "y" the total number tested:

| CANCER TYPE | x/y |
|---|---|
| Ovarian | 1/5 |
| Breast | 3/15 |
| Melanoma | 2/8 |
| Glioma | 12/28 |
| Leukemia | 6/20 |
| Colorectal | 0/10 |
| Renal | 0/5 |
| Prostate | 0/10 |
| Stomach | 0/10 |
| Bronchial | 0/10 |

EXAMPLE 6

As pointed out, supra, SCP-1 is a protein associated with meiosis I, and is involved in chromosome synapsis in particular. Tumor cells are sometimes characterized by aneuploidy. Studies were undertaken to determine whether the aberrant expression of the meiotic protein in somatic cells may be significant for aneuploidy in tumor cells. The subcellular localization of SCP-1 was analyzed by immunofluorescence microscopy using antibodies against SCP-1, monoclonal antibodies against gamma-tubulin, which is a centrosome marker, and human autoimmune sera against centrosomes and centromeres. Subcellular localization was also analyzed with fusion proteins of SCP-1 with green fluorescent proteins (GFP and EGFP, Clontech). The use of polyclonal antibody such as the auto immune sera eliminates the possibility of obtaining a false negative result due to epitope masking by the anti-SCP-1 antibody because the polyclonal sera would contain antibodies specific for different components of the centrosome, not just to tubulin.

To carry out these studies, it was first necessary to determine if antibodies of interest were specific for SCP-1. To asceitain this, CHO cells were transfected with cDNA encoding SCP- 1, using a commercially available vector (pCDNA 3.1). CHO cells had been determined to not express SCP-1 via RT - PCR.

Twenty four hours after transfection, the transfected CHO cells were stained with SC554 antibodies (5 μg/ml), followed by secondary staining with anti-mouse IgG antibodies, labeled with a cyanine dye, CY3 (Mujamdar et al., *Bioconjug. Chem.*, 4(2):105–11 (March–April 1993)).

As a control, CHO cells were transfected with the pcDNA3.1 vector alone.

The cells transfected with SCP-1 stainedin the cytoplasm and nucleus, while the negative controls were not stained at all.

The staining pattern was confirmed using a standard immunochemcial assay and alkaline phosphatase monoclonal anti-alkaline phosphatase (APAAP) method (Cordell et al., *J. Histochem. Cytochem*, 32(2):219–29 (February 1984)).

These experiments were then repeated, using cell line SK-ME-37. This cell line had been shown to express SCP-1. See, e.g., Tureci et al., *Proc. Nat. Acad. Sci. USA* 95:5211–5216 (April 1998), incorporated by reference and Chen et al., *Proc. Nat. Acad. Sci. USA*, 95:6919–6923 (June 1998).

The precise number of stained cells within a stained sample varies and is presented as a percent range rather than a fixed percentage. Exclusive nuclear staining was found in the range of 40–70% of the cells. The nuclear staining pattern ranged from more than 100 small dots, to 20–30 large dots.

A second patten of expression was also observed, where staining was observed in both the nucleus and cytoplasm. This pattern was found in range of 20–60% of the cells.

In order to study the patterns further, the cells were then contacted with antibodies against gamma tubulin, which is a centrosome marker, autoimmune sera against centromeres, and a autoimmune sera against centrosomes.

These follow up assays indicated that the cytoplasmic dots colocalized with gamma tubulin, a marker protein for centrosomes.

EXAMPLE 7

In follow up experiments, vectors were prepared which encoded fusion proteins consisting of green flourescent protein and SCP-1, prepared using standard methods. The vectors were transfected into CHO cells, human epitheloid carcinoma cell line A43 1, and human breast cancer cells, MCF-7.

Expression was found to be localized at the centrosome and centromere. This is in accord with recent studies which have demonstrated that disturbances of centrosome and centromere cycles are observed, frequently, in cancer. (Lingle, et al., *Proc. Nat. Acad. Sci. USA*, 95:2950 (1998); Duesberg, et al., *Science*, 284:2091–2 (1999)). Aberrant expression of SCP-1 in cancer and colocalization to centromeres and centrosomes suggests that SCP-1 has a role in cancer associated dysfunction of these organelles.

EXAMPLE 8

These experiments were designed to study the functional consequences of SCP-1 expression in somatic cells.

cDNA encoding SCP-1 was cloned into an expression plasmid (pVNRL), using standard methods. The resulting expression plasmid, pVRNL-SCP-1, was used to transfect 041 cells, which are immortal, non-neoplastic cells which have been derived from Li-Fraumeni patients and murine NIH 3T3 cells. Both copies of the p53 gene are lost in 041 cells. As controls, both cell types were infected with "empty" expression plasmid pVRNL. The cells were selected in the presence of G418. Following three weeks of culture, the ploidy of G418 resistant cells were assayed by treating the cells with DNA-staining Propidiumiodid (Literatur) and analyzed via flow cytometry using standard methods.

The assay revealed a high percentage of polyploid cells in both 041 cells and NIH 3T3 cells, when transfected with the pVRNL-SCP-1 expression plasmid, suggesting that SCP-1 expression may be associated with acquisition of unstable chromosomal copy numbers, which is characteristic of cancer cells.

EXAMPLE 9

To determine whether SCP-3 is a synaptonemal complex protein its association with SCP-1, a known synaptonemal complex protein, was assayed. To do this, SCP-3A was cloned into pEGFP-N1 and pEGFP-C3 vectors, which allow expression of SCP-3 with an N-terminal or C-terminal green flourescent protein tag in eukaryotic cells. The fusions of full-length SCP-3 with green fluorescent protein (EGFP) permitted direct studies on SCP-3 by immunofluorescence microscopy.

The constructs SCP-1-pcDNA3 and SCP-3A-pEGFP were cotransfected into human breast cells (MCF-7), CHO cells, human epitheloid carcinoma cells (A431), and melanoma cells (SK-Mel37) seeded in chamber slides with Fugene. The following day the cells were fixed with 2% PFA/0.01% saponin/PBS for 1 hr at room temperature. The cells were incubated with the SCP-1 specific mAb SC554 and SCP-1 bound with SC554 was detected with a rhodamine-conjugated second antibody. All antibodies were diluted in 0.025% saponin/PBS. The distribution pattern of SCP-1 and SCP-3 was the same in all the cell types.

SCP-1 and SCP-3 were found to colocalize, as determined by a Confocal laser microscopy analysis. The SCP-1 pattern in cells transfected with both SCP-1 and SCP-3 differed from the pattern detected in cells expressing only SCP-1 in that SCP-1 in the cotransfected cells was localized in nuclear dots located in the nucleoplasma outside the nucleoli rather than in the centrosomes.

To further investigate the nature of the nuclear dots, the cells were reacted with a panel of human autoimmune sera having defined antibody-specificities that correlate with the clinical course of particular diseases in patients. An example of such sera is from patients with primary biliary cirrhosis which contain antibodies that react with SP100, an autoantigen found predominantly in patients with primary biliary cirrhosis. The SP100 specific sera of these patients reacts with the nuclear dots containing the SCP-1 and SCP-3

The nucleoproteins SP100 and PML, a transformation and cell growth suppressing protein aberrantly expressed in promyelocytic leukemia cells, were recently shown to colocalize in dot like nuclear bodies (Sternsdorf et al., *Scan. J. Immunol.*, 42(2):257–68 (August 1995); Sternsdorf et al, *J. Cell Biol.*, 139(7):1621–1634 (December 1997); and Giotzinger et al., *Eur. J. Biochem.*, 238(2):554–60 (June 1996)). These nuclear bodies (NBs) represent the best studied example of a defined nuclear substructure the integrity of which is compromised in certain human diseases, including leukemia, neurodegenerative disorders and viral infection. Recent progress has underscored the unexpectedly broad involvement of NB constituents in the control of cell growth, gene regulation and apoptosis in both pathological and normal contexts (see e.g., Seeler & Dejean, *Curr. Opin. Genet. Dev.*, 9(3):362–367 (June 1999) and Zuchner et al., *Hepatology*, 26(5):1123–30 (November 1997)).

The foregoing examples demonstrate several features of the invention. These include isolated nucleic acid molecules which have complementary sequences that hybridize to at least one of SEQ ID NOS: 1, 2, 4, and 7 under stringent conditions. In a preferred embodiment, these isolated nucleic acid molecules encode human SCP2 or SCP-3. Stringent conditions refer to conditions at least as stringent as overnight hybridization in 5×SSC buffer, including 2×Denhard's solution, using a 300 base pair $^{32}$P labelled probe (20 ng/ml of solution) at 65° C., followed by 2 washes of 15 minutes each, using 1×SSC per wash at 65° C. Also a part of the invention are expression vectors which comprise any of the foregoing sequences, operably linked to a promoter. Such expression vectors, as well as the isolated nucleic acid molecules themselves, may be used to produce recombinant eukaryotic or prokaryotic cells, which have been transformed or transfected with the isolated nucleic acid molecules or expression vectors of the invention. Also a part of the invention are diagnostic methods for determining presence of transformed cells, such as cancer cells, in a sample. The examples show that there is a family of SCP genes which are expressed in cancer cells. Hence, the invention involves, inter alia, detecting protein encoded by the nucleic acid molecules or mRNA such as those described in a sample taken from a source other than testis, wherein presence of either or both of these is indicative of a pathology, such as cancer or some other type of transformed cells. Exemplary of the type of diagnostic assays which can be carried out are amplification assays such as polymerase chain reaction, or immunoassays. It is especially preferred to assay for a determination of prostate cancer, breast cancer, melanoma, ovarian cancer, renal cell carcinoma, or glioma. Preferably, the oligonucleotides of SEQ ID NOS: 5, 6, 8, 9, 10, 11, 13, or 14 are used. Any sequence which hybridizes to SEQ ID NOS: 1, 2, 4 , 7 or 12 ('205), can be used.

The SCP proteins, as indicated, have been associated, exclusively, with meiosis. As a rule, cells other than germ cells do not undergo meiosis. Hence, the expression of SCP proteins such as SCP-1 or SCP-3 in a context other than germ cells undergoing meiosis is clearly an indication of an abnormality. It is believed that expression of SCP proteins such as SCP-1 or SCP-3 may contribute to the genetic instability of cancer cells, leading to abnormalities such as aneuploidy, manifesting the phenomenon in early neoplastic change. One aspect of the invention, then, is a method for determining presence of an abnormal condition by assaying for an SCP protein, or a peptide derived from the protein, wherein the presence of the protein at all, or an abnormal level of the protein (which may include its presence), is indicative of an abnormality, such as cancer. There are many ways to carry out this type of assay. For example, as indicated herein, antibodies to the protein were found in patient samples. One can assay for these antibodies using, e.g., the methodology described herein, or by using a purified SCP protein or antigenic fragment thereof, and so forth. One can also assay for the protein itself, using antibodies, which may be isolated from samples, or generated using an SCP protein and standard techniques. This antibodies can then be labelled, if desired, and used in standard immunoassays.

Similarly, any and all nucleic acid hybridization systems can be used, including amplification assays, such as PCR, basic probe hybridization assays, and so forth. The antibodies, such as polyclonal antibodies, monoclonal antibodies, the hybridomas which produce them, recombinantly produced antibodies, binding fragments of these, hybridization kits, DNA probes, and so forth, are all additional features of the invention.

Any of these assays can also be used in progression/regression studies. Since it is clear that a low or non-existent level of expression of SCP protein is found in normal cells, one can monitor the course of abnormality involving expression of SCP, simply by monitoring levels of the protein, its expression, and so forth using any or all of the methods set forth supra.

It should be clear that these methodologies may also be used to track the efficacy of a therapeutic regime. Essentially, one can take a baseline value for the SCP protein or proteins being tested, using any of the assays discussed supra, administer a given therapeutic agent, and then monitor levels of the protein thereafter, observing changes in SCP levels as indicia of the efficacy of the regime. Further approaches to this aspect of the invention, inter alia, detection of T cells which recognize SCP 3 or complexes of SCP-3 derived peptides and MHC molecules, via $^{51}$Cr release, TNF production, ELISPOT, or by the use of soluble multimeric complexes of peptides and MHC molecules.

The identification of SCP proteins as being implicated in pathological conditions such as cancer also suggests a number of therapeutic approaches to such conditions. The experiments set forth supra establish that antibodies are produced in response to expression of the protein, suggesting its use as a vaccine. Hence, a further embodiment of the invention is the treatment of conditions which are characterized by aberrant or abnormal levels of one or more SCP proteins, via immunotherapeutic approaches. One of these approaches is the administration of an amount of an SCP protein, or an immunogenic peptide derived from the protein in an amount sufficient to provoke or augment an immune response. The protein or peptide may be combined with one or more of the known immune adjuvants, such as saponins, GM-CSF, interleukins, and so forth. If the peptides are too small to generate a sufficient antibody response, they can be coupled to the well known conjugates used to stimulate responses.

Similarly, the immunotherapeutic approaches include administering an amount of inhibiting antibodies sufficient to inhibit the SCP protein. These antibodies may be, e.g., antibodies produced via any of the standard approaches elaborated upon supra.

T cell responses may also be elicited by using peptides derived from the SCP proteins which then complex, non-covalently, with MHC molecules, thereby stimulating proliferation of cytolytic and helper T cells against any such complexes in the subject. It is to be noted that the T cells may also be elicited in vitro using immune responsive cells such as dendritic cells, lymphocytes, or any other immune responsive cells, and then reperfused into the subject being treated.

Note that the generation of T cells and/or antibodies can also be accomplished by administering cells, preferably treated to be rendered non-proliferative, which present relevant T cell or B cell epitopes for response. These may be treated to present the peptide via pulsors, or transformation/transfections to express the peptide.

The therapeutic approaches may also include gene therapies, wherein an antisense molecule, preferably from 10 to 100 nucleotides in length, is administered to the subject either "neat" or in a carrier, such as a liposome, to facilitate incorporation into a cell, followed by inhibition of expression of the protein. Such antisense sequences may also be incorporated into appropriate vaccines, such as in viral vectors (e.g., Vaccinia), bacterial constructs, such as variants of the well known BCG vaccine, and so forth.

An additional DNA based therapeutic approach is the use of a vector which comprises one or more nucleotide sequences, preferably a plurality of these, each of which encodes an immunoreactive peptide derived from the expressed proteins. One can combine these peptide expressing sequences in all possible variations, such as one from each protein, several from one or more protein and one from each of the additional proteins, a plurality from some and none from others, and so forth.

The subcellular localization of SCP-1 is important as it has a specific function in meiosis I and is involved in chromosome synapsis. The aberrant expression of these meiotic protein in somatic cells is significant for tumor cell aneuploidy and thus SCP-1 is useful as a prognostic marker.

The association of SCP-1 and SCP-3 with nuclear bodies that are also associated with other antigens displaying a high correlation with disease, e.g., SP100 an autoantigen predominantly in patients with biliary cirrhosis , supports a role for SCP-1 and SCP-3 in a variety of cellular abnormalities. In view the disclosure supra, inhibitors of SCPs, e.g., antibodies and small molecules as well as antagonists of SCP-1 in general, are useful in detection, prevention or treatment of conditions characterized by abnormal expression of SCPs.

The association of aberrant SCP-1 and SCP-3 expression with aneuploidy and the discovery of the association of SCP-1 and SCP-3 with nuclear bodies that are also associated with nucleoproteins associated with particular pathogenic disorders, suggests a number of approaches for screening a sample for possibly containing cells with an aberrant chromosome number, or for determining if a sample contains abnormal cells, which would be indicative of the possibility of an pathogenic disorder. For example a cell sample other than testis cells could be assayed for nuclear bodies associated with an SCP, e.g., SCP-1 or SCP-3, and could also assayed for the association of these nuclear bodies with an agent that is specific for a marker for a particular pathogenic disorder, e.g., cancer, cirrhosis or leukemia. Preferably, the second marker is Sp 100 or PML or both, which are nucleoproteins associated with, respectively, primaly biliary cirrhosis and promyelocytic leukemia, and are found predominantly in the cells of patients suffering from these disorders. The association of SCP-1 and SCP-3 with nuclear bodies could be assayed by contacting the cell sample with an antibody specific for SCP-1 or SCP-3 and determining antibody binding. The antibody may be a labeled antibody, e.g., labelled with a fluorescent marker or a radioactive tag, or the antibody may be detected with a second labeled antibody specific for antibody directed against the SCP. The sample may be a tissue sample or a cell culture sample. The cell sample assayed may be one that does not contain meiotic cells.

Another aspect of the invention is a screening method for determining if a substance binds to SCPs, particularly SCP-1 or SCP-3. Such substances may be detected by contacting a substance with an SCP-1, or SPC-3, containing sample for sufficient time for said substance to bind to the SCP-1 or SCP-3 in the sample and then determining if the substance is bound to the SCP. Binding may be determined using an antibody directed against the substance assayed. Alternatively, the SCP can be immobilized on a matrix, a sample may be contacted with the bound SCP and the substances which bind to the SCP may be eluted and isolated. Those of skill in the art appreciate that many methods may be used to elute the bound substances, e.g, with a competing free SCP or with a competing antibody or by varying the ionic character of the washes.

Another aspect of the invention is a method for identifying agents which affect the association of SCPs, particularly SCP-1 and SCP-3 with nuclear bodies. For example, a cell sample expressing an SCP, e.g., SCP-1 or SCP-3, may be contacted with an agent to be tested for a sufficient time for the agent to affect the association of the SCP with the nuclear bodies in the cells. The association of the SCP with the nuclear bodies in treated cells is then compared to the association of the SCP with the nuclear bodies in untreated cells. A difference in the association of the SCPs with the nuclear bodies would be indicative of an agent that affects the association of the SCP with nuclear bodies. The agent may increase or decrease the amount of the SCP associated with the nuclear bodies or it may increase or decrease the number of nuclear bodies that associate with the SCP.

Other features of the invention will be clear to the skilled artisan, and need not be repeated here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

What is claimed is:

1. A method for determining presence of a transformed cell, comprising assaying a sample of cells taken from tissue other than testis for expression of a synaptonemal complex protein ("SCP") gene, wherein expression thereof is indicative of transformed cells in said sample.

2. The method of claim 1, comprising determining said expression with at least one of SEQ ID NOS: 1, 2, 4, 7 or 12.

3. The method of claim 1, comprising determining said expression with at least one of SEQ ID NOS: 5, 6, 8, 9, 10, 11, 13, or 14.

4. The method of claim 1, wherein said transformed cell is an ovarian cancer, prostate cancer, melanoma, renal cancer, or breast cancer cell.

5. The method of claim 1, comprising determining an antibody specific for SCP-2 gene or an SCP-3 gene.

6. The method of claim 1, further comprising deteimining presence of mRNA for said SCP-2 gene or said SCP-3 gene.

7. The method of claim 6, comprising determining presence of mRNA via polymerase chain reaction.

8. The method of claim 1, comprising assaying said sample for an SCP-2 protein or an SCP-3 protein.

9. The method of claim 8, comprising assaying said sample via an immunoassay.

10. The method of claim 1, wherein said transformed cell is a cancer cell.

11. The method of claim 10, wherein said cancer cell is a prostate cancer renal cancer cell, a glioma, ovarian, or a breast cancer cell.

12. The method of claim 1, comprising amplifying RNA which codes for said SCP-2 or SCP-3 protein.

13. The method of claim 1, wherein said amplifying comprises carrying out polymerase chain reaction.

14. The method of claim 1, comprising contacting said sample with a nucleic acid molecule which specifically hybridizes to a nucleic acid molecule which codes for or expresses said SCP-2 or SCP-3 protein.

* * * * *